United States Patent [19]

Tsunekawa et al.

[11] Patent Number: 4,878,971

[45] Date of Patent: Nov. 7, 1989

[54] METHOD OF CONTINUOUSLY ASSEMBLING CHEMICAL ANALYSIS SLIDES

[75] Inventors: Yuzo Tsunekawa; Yukio Ishida; Tatsuo Shiino, all of Kanagawa, Japan

[73] Assignee: Fuji Photo Film Co., Ltd., Kanagawa, Japan

[21] Appl. No.: 148,834

[22] Filed: Jan. 27, 1988

[30] Foreign Application Priority Data

Jan. 28, 1987 [JP] Japan .................................. 62-18111

[51] Int. Cl.⁴ ........................ B32B 31/10; B32B 31/08
[52] U.S. Cl. ...................................... 156/70; 156/252; 156/324; 422/66; 428/78; 428/136; 436/44
[58] Field of Search .......................... 156/70, 252, 324; 422/66, 104; 428/78, 136; 436/44, 46

[56] References Cited

U.S. PATENT DOCUMENTS

| | | | |
|---|---|---|---|
| 3,036,894 | 5/1962 | Forestiere | 422/66 X |
| 3,620,678 | 11/1971 | Guigan et al. | 422/66 |
| 4,071,315 | 1/1978 | Chateau | 422/66 X |
| 4,650,217 | 3/1987 | Ehrlund | 428/136 X |
| 4,685,880 | 8/1987 | Meouro et al. | 422/66 X |

FOREIGN PATENT DOCUMENTS 53-21677  7/1978  Japan .
55-164356 12/1980 Japan .
61-51570  3/1986  Japan .

Primary Examiner—Robert A. Dawson
Attorney, Agent, or Firm—Sughrue, Mion, Zinn, Macpeak & Seas

[57] ABSTRACT

A chemical analysis slide includes at least two plastic sheets superposed one on another and bonded together, and a chemical analysis film sandwiched therebetween. In a method of continuously assembling such chemical analysis slides, while at least two plastic sheets in continous lengths are conveyed in the longitudinal direction thereof, a plurality of chemical anaylsis films are sandwiched between the plastic sheets at predetermined intervals, the plastic sheets are bonded together at a portion circumscribing each of the chemical analysis films sandwiched therebetween to form a sheet assembly and individual chemical analysis slides are cut out from the sheet assembly. At least one of the sheets in continuous lengths is provided with a plurality of slits extending in the transverse direction of the sheet at regular intervals at the remaining portions of the sheet which do not form a part of the chemical analysis slide.

3 Claims, 5 Drawing Sheets

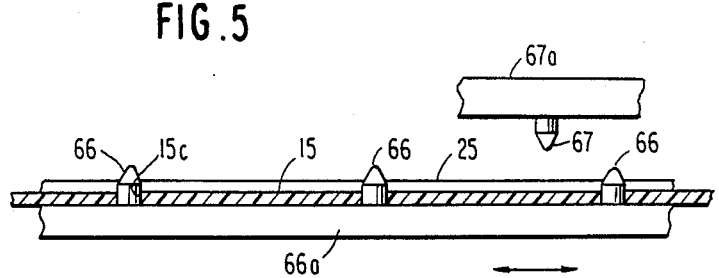
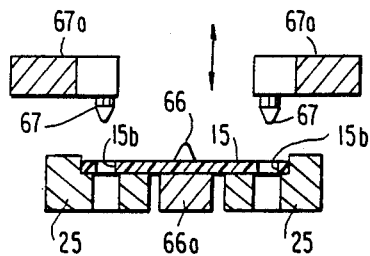
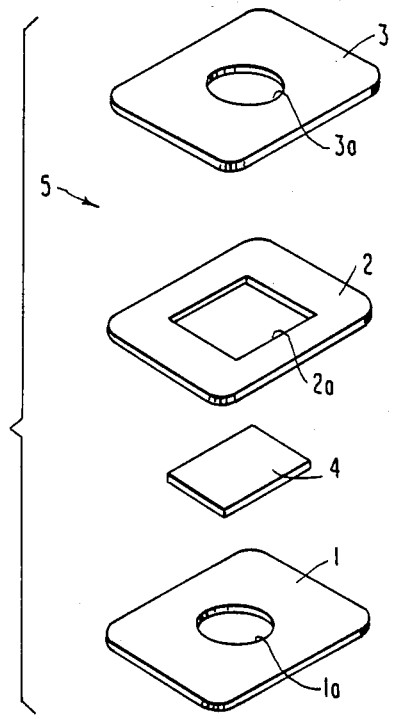

METHOD OF CONTINUOUSLY ASSEMBLING CHEMICAL ANALYSIS SLIDES

FIELD OF THE INVENTION

This invention relates to a method of assembling chemical analysis slides for chemically analyzing a sample liquid.

DESCRIPTION OF THE PRIOR ART

There has been put into practice a dry type chemical analysis slide for analyzing chemical components or material components such as glucose, bilirubin, urea, nitrogen or the like contained in a sample liquid, e.g., body fluid, by simply depositing a droplet of the liquid sample on the slide. See, for example, Japanese Patent Publication No. 53(1978)-21677 and Japanese Unexamined Patent Publication No. 55(1980)-164356. When analyzing a chemical component or the like in a sample liquid by use of such a chemical analysis slide, a small amount of sample liquid is measured and deposited on the chemical analysis film of the chemical analysis slide, and the chemical analysis slide bearing thereon the sample liquid is incubated for a predetermined time in an incubator, thereby promoting color reaction. Then measuring light containing a wavelength predetermined according to the combination of the component in the sample liquid and the reagent contained in the reagent layer on the chemical analysis film is projected onto the chemical analysis slide and the reflection density of the chemical analysis film is measured.

For example, as shown in FIG. 7, the chemical analysis slide 5 comprises a mount base 1 formed of a rectangular plastic sheet having a reflection density measuring opening 1a through which the reflection density of the chemical analysis film is measured, a mount frame 2 formed of a rectangular plastic sheet having a chemical analysis film holding opening 2a larger than the reflection density measuring opening 1a in size, a chemical analysis film 4 held in the chemical analysis film holding opening 2a, and a mount cover 3 formed of a rectangular plastic sheet having a sample liquid depositing opening 3a through which a sample liquid is deposited on the chemical analysis film 4. The mount base 1, the mount frame 2 and the mount cover 3 are bonded together with the mount frame 2 being sandwiched between the mount base 1 and the mount cover 3 and the chemical analysis film 4 being placed in the chemical analysis film holding opening 2a.

There has been known a method of continuously assembling a plurality of such chemical analysis slides in order to increase assembling efficiency of the slides. In the known method, plastic sheets in continuous lengths are unrolled from respective rolls, and are respectively formed with the reflection density measuring opening 1a, the chemical analysis slide holding opening 2a and the sample liquid depositing opening 3a. The sheets are superposed one on another and bonded together with the chemical analysis films 4 being held in the holding openings 2a, and then the chemical analysis slides are stamped to a predetermined shape from the assembly thus obtained. However, this method is disadvantageous in that since the sheets are conveyed over a relatively large distance in the form of long strips, the sheets are apt to meander and to be stretched and when the sheets meander and/or are stretched, the optical density measuring openings 1a, the chemical analysis film holding openings 2a and the sample liquid depositing openings 3a cannot be correctly aligned with each other when the sheets are bonded together and/or warpage can be produced in the products obtained.

However, when the plastic sheets are cut into a length of one or several chemical analysis slides in advance and then the chemical analysis films are mounted thereon as disclosed in Japanese Unexamined Patent Publication No. 61(1986)-51570 in order to obviate the problems described above, the assembling apparatus must handle the sheet pieces cut out from the sheets one by one, and accordingly, the apparatus is inherently complicated and it becomes difficult to increase the assembling speed.

SUMMARY OF THE INVENTION

In view of the foregoing observations and description, the primary object of the present invention is to provide a method of continuously assembling chemical analysis slides in which chemical analysis slides having correctly aligned reflection density measuring openings, chemical analysis slide holding openings and sample liquid depositing openings and free from warpage can be assembled without being affected by meander or stretch of the plastic sheets in continuous lengths.

In accordance with the present invention, there is provided a method of continuously assembling chemical analysis slides each including at least two plastic sheets superposed one on another and bonded together, and a chemical analysis film sandwiched therebetween. In accordance with the method, while at least two plastic sheets in continuous lengths are conveyed in the longitudinal direction thereof, a plurality of chemical analysis films are sandwiched between the plastic sheets at predetermined intervals, the plastic sheets are bonded together at a portion circumscribing each of the chemical analysis films sandwiched therebetween to form a sheet assembly and individual chemical analysis slides are cut out from the sheet assembly. At least one of the sheets in continuous lengths is provided with a plurality of slit means extending in the transverse direction of the sheet at regular intervals at the remaining portions of the sheet which do not form a part of the chemical analysis slide.

The slit means formed in said at least one sheet absorb stretch and/or meander of the sheet to permit precise location of the sheets with respect to each other, and accordingly, warpage is not be produced in the finished products. Further, it is preferred that said at least one sheet be provided with a plurality of locating holes formed at the remaining portions, at least one between each pair of slit means, in order to more precisely locate the sheets with respect to each other.

BRIEF DESCRIPTION OF THE DRAWINGS

FIGS. 5 and 6 are cross-sectional views for illustrating the operation of a part of the apparatus, and FIG. 7 is an exploded perspective view showing a chemical analysis slide to be assembled in accordance with the method of the present invention.

DESCRIPTION OF THE PREFERRED EMBODIMENT

Figure 1:
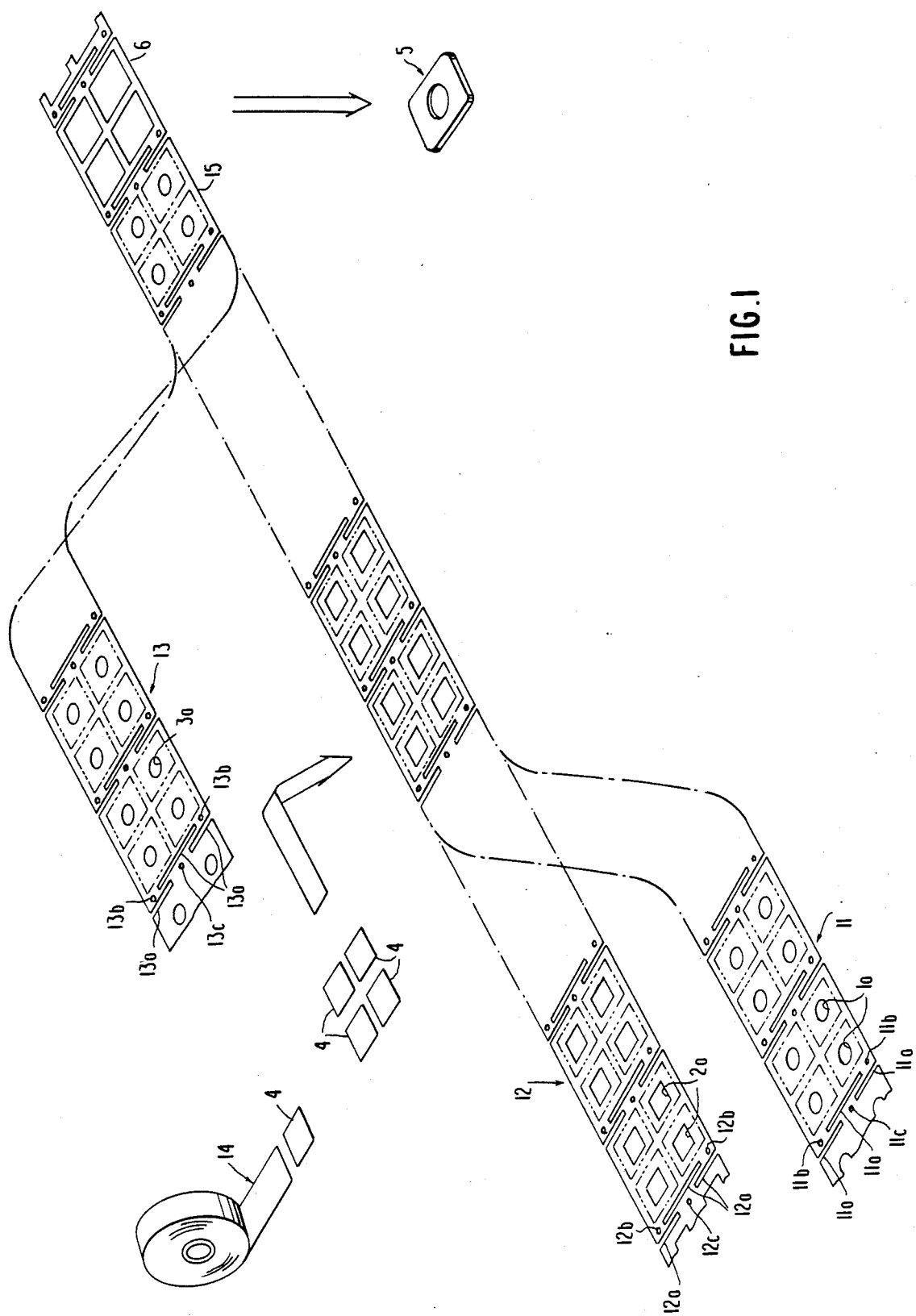
FIG. 1 is a schematic perspective view showing chemical analysis slide assembling steps in accordance with an embodiment of the present invention.

In accordance with an embodiment of the present invention, as shown in FIG. 1, first, second and third plastic sheets 11, 12 and 13 in continuous lengths respectively for forming mount bases, mount frames and mount covers are supplied from rolls (not shown), for instance. The first plastic sheet 11 is provided with a plurality of openings arranged in two rows extending in the longitudinal direction of the sheet 11 and numbers of columns perpendicular to the rows. The openings are for forming the reflection density measuring openings 1a in finished products described above in conjunction with FIG. 7, as will become apparent later, and accordingly, are indicated at 1a in the drawings and will be referred to as "the reflection density measuring openings 1a", hereinbelow. Similarly, the second and third plastic sheets 12 and 13 are respectively provided with a plurality of openings arranged in two rows extending in the respective longitudinal directions thereof and numbers of columns perpendicular to the rows. The openings are respectively for forming the chemical analysis film holding openings and the sample liquid depositing openings in finished products described above in conjunction with FIG. 7, and accordingly, are indicated at 2a and 3a in the drawings and will be referred to as "the chemical analysis film holding openings 2a" and "the sample liquid depositing openings 3a", hereinbelow. The first to third plastic sheets 11 to 13 are cut along the double dotted chain lines after being bonded together to form individual chemical analysis slides. The plastic sheets 11 to 13 are intermittently conveyed at regular intervals by a conveying means which may be of a feed pin system, for instance. The reflection density measuring openings 1a are divided into groups of four each formed of two adjacent columns, and three transverse slits 11a are formed in the first plastic sheet 11 between each pair of adjacent groups, two of the three slits 11a extending inwardly from opposite edges of the first plastic sheet 11 in alignment with each other and the other slit 11a extending in parallel to the other two slits 11a at the middle of the sheet 11. That is, numbers of sheet segments each for forming four mount bases are linked together with the three slits 11a intervening between each pair of adjacent sheet segments. A pair of locating holes 11b are provided near the edges of the sheet 11 between each pair of adjacent sheet segments and perforations 11c for feeding the film 11 are provided along the longitudinal axis of the sheet 11 each between each pair of adjacent sheet segments. Similarly, the chemical analysis film holding openings 2a are divided into groups of four each formed of two adjacent columns, and three transverse slits 12a are formed in the second plastic sheet 12 between each pair of adjacent groups, two of the three slits 12a extending inwardly from opposite edges of the second plastic sheet 12 in alignment with each other and the other slit 12a extending in parallel to the other two slits 12a at the middle of the sheet 12. That is, numbers of sheet segments each for forming four mount frames are linked together with the three slits 12a intervening between each pair of adjacent sheet segments. A pair of locating holes 12b are provided near the edges of the sheet 12 between each pair of adjacent sheet segments and perforations 12c for feeding the film 12 are provided along the longitudinal axis of the sheet 12 each between each pair of adjacent sheet segments. Similarly, the sample liquid depositing openings 3a are divided into groups of four each formed of two adjacent columns, and three transverse slits 13a are formed in the third plastic sheet 13 between each pair of adjacent groups, two of the three slits 13a extending inwardly from opposite edges of the third plastic sheet 13 in alignment with each other and the other slit 13a extending in parallel to the other two slits 13a at the middle of the sheet 13. That is, numbers of sheet segments each for forming four mount covers are linked together with the three slits 13a intervening between each pair of adjacent sheet segments. A pair of locating holes 13b are provided near the edges of the sheet 13 between each pair of adjacent sheet segments and perforations 13c for feeding the film 13 are provided along the longitudinal axis of the sheet 13 each between each pair of adjacent sheet segments. The chemical analysis films 4 are obtained by cutting a rolled chemical analysis film sheet 14 of a predetermined width in predetermined lengths. The slits 11a, 12a and 13a accommodate difference in position among the sheet segments in the respective plastic sheets and stretch of the sheets 11, 12 and 13, and prevent meander of the sheets 11, 12 and 13.

While the first and second plastic sheets 11 and 12 are conveyed, the second plastic sheet 12 is superposed on the first plastic sheet 11 and the reflection density measuring openings 1a in the first plastic sheet 11 are aligned with the chemical analysis film holding openings 2a in the second plastic sheet 12, and then the sheets 11 and 12 are bonded together. More particularly, feed pins are inserted into the perforations 11c and 12c of the first and second plastic sheets 11 and 12 to convey the sheets 11 and 12 in the superposed state. Further, by inserting the feed pins into the perforations, the sheets 11 and 12 are substantially aligned with each other. When the sheets 11 and 12 are bonded together, locating pins are inserted into the locating holes 11b and 12b to bring corresponding sheet segments of the respective sheets 11 and 12 in precise alignment with each other, and then the sheets 11 and 12 are bonded together by means of adhesive, ultrasonic welding or the like. Thus a sheet assembly in a continuous length having spaces for accommodating therein chemical analysis films 4 defined by the chemical analysis film holding openings 2a in the second plastic film 12 is formed.

While the sheet assembly is further conveyed by the feed pins, the chemical analysis films 4 are inserted into the spaces defined by the chemical analysis film holding openings 2a by suitable means such as a pick-and-place apparatus. Thereafter, the third plastic sheet 13 is superposed on the sheet assembly on the second plastic sheet side while they are conveyed, and then they are bonded together Thus, a sheet assembly 15 in a continuous length having therein the chemical analysis films 4 accommodated in the openings 2a and held therein by the third plastic film 13 is obtained. The sheet assembly 15 is stamped along the double dotted chain lines in FIG. 1 to produce a plurality of individual chemical analysis slides 5. Also when the third plastic sheet 13 is bonded to the second plastic sheet and the individual chemical analysis slides 5 are cut out from the sheet assembly 15, locating pins are inserted into the locating holes for precise location of the plastic sheets with respect to each other or to the stamping means. During the steps described above, the slits 11a, 12a and 13a between the sheet segments of the respective plastic sheets 11, 12 and 13 absorb stretch and/or meander of the sheets 11, 12 and 13 to permit precise location of the sheets 11, 12 and 13 by the locating pins. Thus, the openings 1a, 2a and 3a are correctly aligned with each other in the finished products and since none of the sheets 11, 12 and 13 is stretched when they are actually bonded together, warpage is not be produced in the finished products. The remainder 6 may be cut in suitable lengths and thrown away.

An example of an apparats for carrying out the method described above will be described with reference to FIGS. 2 to 6, hereinbelow.

Figure 2:
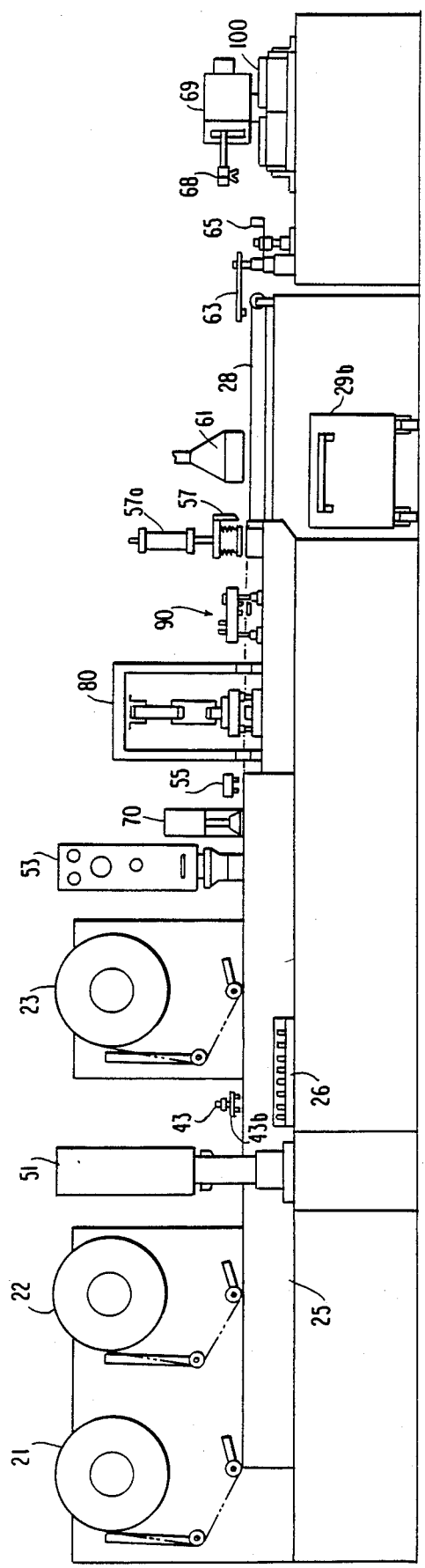
FIG. 2 is a front elevational view of an apparatus for carrying out the assembling steps shown in FIG. 1.

This apparatus has a first conveying passage 25 along which the first to third plastic sheets 11, 12 and 13 are conveyed from the left to the right as seen in FIG. 2. Above the first conveying passage 25, there are disposed first to third sheet supply reels 21, 22 and 23 for respectively feeding the first to third plastic sheets 11 to 13 to the first conveying passage 25. A first ultrasonic welder 51 is provided between the second and third reels 22 and 23. The second plastic sheet 12 fed to the first conveying passage 25 from the second sheet supply reel 22 is superposed on thefirst plastic sheet 11 fed to the first conveying passage 25 from the first sheet supply reel 21, and aligned sheet segments of the first and second plastic sheets 11 and 12 are welded together by the first ultrasonic welder 51.

Figure 3:
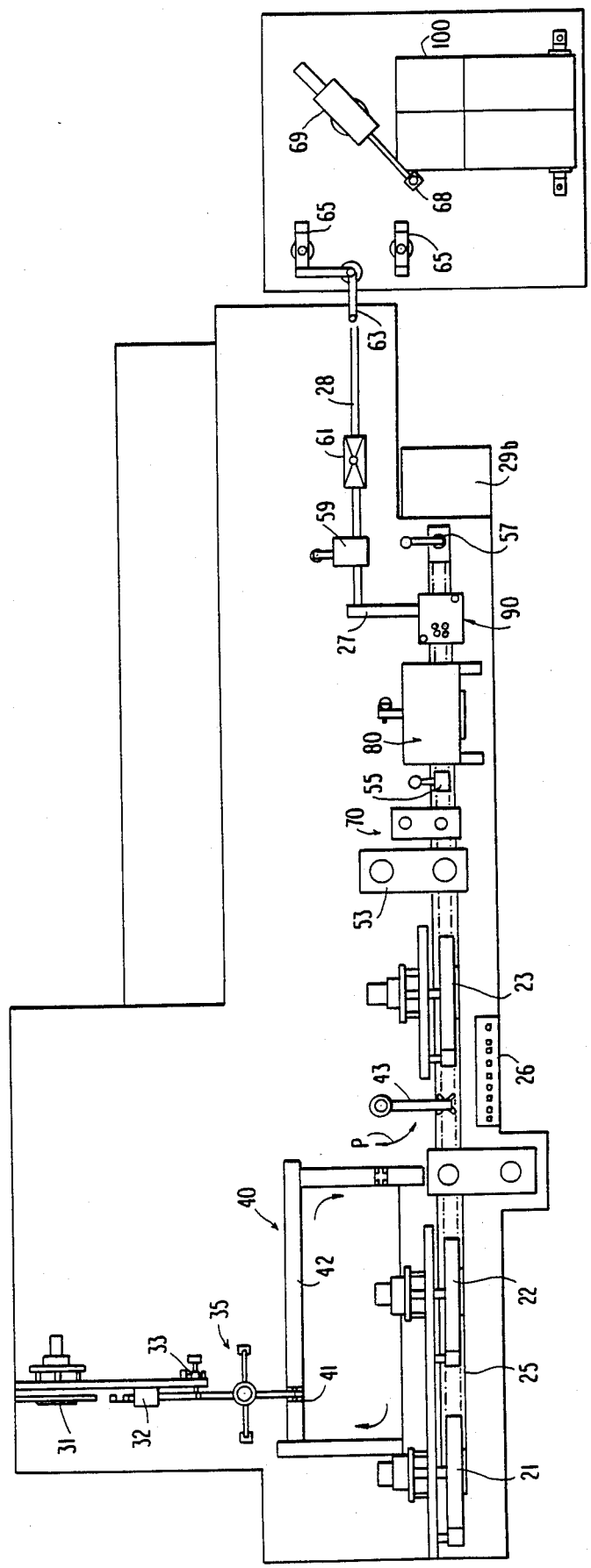
FIG. 3 is a plan view of the apparatus shown in FIG. 2.

Subsequently, the chemical analysis films 4 are inserted into the chemical analysis film holding openings 2a of the second plastic sheet 12. This insertion of the films 4 is accomplished simultaneously for the four chemical analysis film holding openings 2a in each sheet segment and will be described in detail with reference to FIG. 4. The chemical analysis film sheet 14 is rolled around a fourth reel 31 (FIG. 3). After being unrolled from the fourth reel 31, the chemical analysis film sheet 14 is inspected by a sample inspection device 32 and then cut in predetermined lengths by a cutter 33 to form chemical analysis films 4 of a predetermined size. The chemical analysis films 4 are placed on a pallet 41 of a pallet conveying section 40 by a high speed transfer means 35.

Figure 4:
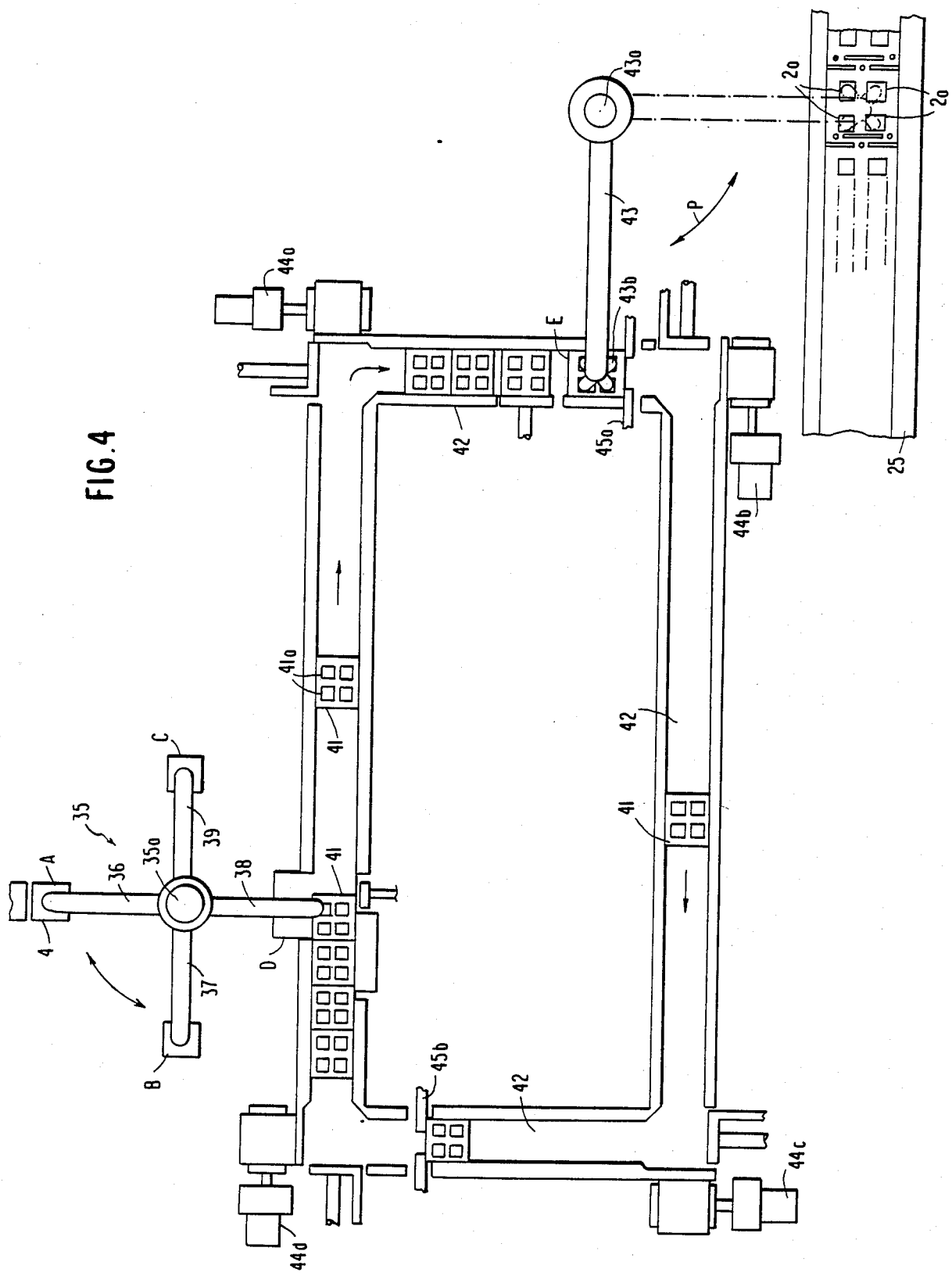
FIG. 4 is an enlarged plan view showing in more detail a part of the apparatus.

The high speed transfer means 35 has four arms 36 to 39 which are rotatable back and forth about a shaft 35a by 90°. Each of the arms 36 to 39 is provided with a suction cup on the free end thereof. The chemical analysis film 4 in A position in FIG. 4 is picked up by the suction cup on the arm 36 and is transferred to B position by 90° counterclockwise rotation of the arm 36. At the same time, the film 4 in B position is transferred to the pallet 41 in D position by 90° counterclockwise rotation of the arm 37, and the arms 38 and 39 respectively in D position and C position are moved to C position and A position, respectively. Thereafter, the high speed transfer means 35 is rotated in the clockwise direction by 90°, and the film 4 fed to A position is picked up by the suction cup on the arm 39 at this time, and the film 4 in C position is transferred to the pallet 41 in D position by the arm 38. At the same time, the arms 36 and 37 are returned to A position and B position, respectively. Thus, the films 4 successively fed to A position are successively transferred to the recesses 41a of the pallets 41 successively moved to D position. Rejected films 4 detected by the sample inspection device 32 are removed so as not to be transferred to the pallet 41. The pallet conveying section 40 includes a pallet conveying passage 42 in the form of a rectangular loop. A plurality of the pallets 41 are placed on a conveyor driven by driving motors 44a to 44d and conveyed along the conveying passage 42 in the clockwise direction. Each pallet 41 has four recesses 41a each for receiving one chemical analysis film 4, and when all the recesses 41a are loaded with the films 4 in D position by the high speed transfer means 35, the pallet 41 is conveyed in the clockwise direction along the passage 42 to E position. A stopper 45a stops the pallet 41 in E position. Above E position, there is provided a sample transfer arm 43 which is rotatable back and forth about a shaft 43a as shown by arrow P and is provided with four suction cups 43b on the free end thereof. The films 4 on the pallet 41 in E position are picked up by the suction cups 43b on the sample transfer arm 43. When the sample transfer arm 43 is rotated to the position shown by the broken line in FIG. 4, the films 14 carried by the suction cups 43b are positioned above the sheet assembly, that is, the first and second sheets 11 and 12 bonded together, on the first conveying passage 25. Then the arm 43 is moved downward and the films 4 are released from the suction cups 43b to be placed in the four chemical analysis film holding openings 2a of a segment of the sheet assembly. Thereafter, the pallet 41 is clockwisely moved along the passage 42 and returned to D position.

After the chemical analysis film holding openings 2a are thus loaded with the chemical analysis films 4, the sheet assembly is further conveyed along the first conveying passage 25 and the third plastic sheet 13 wound around the third reel 23 is superposed on the sheet assembly on the second sheet side. A second ultrasonic welder 53 (FIGS. 2 and 3) welds the third plastic sheet 13 to the second plastic sheet 12 at portions circumscribing the chemical analysis film holding openings 2a. In this manner, there is formed said sheet assembly 15 (FIG. 1) comprising a plurality of sheet segments connected together with three slits intervening between each pair of sheet segments, each sheet segment including four chemical analysis slides contiguous to each other.

The sheet assembly 15 is further conveyed rightward as seen in FIG. 2 along the first conveying passage 25 to be positioned below a film height inspector 70. The film height inspector 70 inspects the height of the chemical analysis films 4 in each sheet segment, thereby inspecting whether the chemical analysis films 4 are correctly loaded in the respective chemical analysis film holding openings 2a.

After the film height inspection, the sheet assembly 15 is conveyed to be positioned below a film loading inspector 55. The film loading inspector 55 detects whether each chemical analysis film holding opening 2a is loaded with a chemical analysis film 4 by, for instance, detecting whether light can travel through the aligned openings 1a, 2a and 3a without interference.

After checking whether each chemical analysis film holding opening 2a is loaded with the film 4, the sheet assembly 15 is cut along the double dotted chain lines shown in FIG. 1 by a stamping press 80, whereby four chemical analysis slides 5 are produced for each sheet segment. In this particular embodiment, the stamping press 80 is of a push-back type and the products or the chemical analysis slides 5 once stamped out from the sheet assembly 15 are returned to the remainder 6 of the sheet assembly 15 to be held thereby. The products thus obtained are conveyed to a product take-out device 90 carried by the remainder 6. The product take-out device 90 separates acceptable products and non-acceptable products from the products carried by the remainder 6 and pushes the acceptable product onto a second conveying passage 27. The remainder 6 of the sheet assembly 15 is cut in suitable lengths by a cutter 57 driven by a cylinder 57a and is thrown into a disposal box 29.

The method of conveying the sheet assembly 15 along the first conveying passage 25 by the feed pins and the method of locating the same in predetermined positions by the locating pins are described with reference to FIGS. 5 and 6, hereinbelow. FIG. 5 is a fragmentary cross-sectional view of a part of the first conveying passage 25 together with the sheet assembly 15 taken along a vertical plane extending in the sheet conveying direction and FIG. 6 is a fragmentary cross-sectional view of the same taken along vertical plane perpendicular to the sheet conveying direction.

A feed pin support 66a is provided at the middle of the first conveying passage 25 for sliding motion in the longitudinal direction of the first conveying passage 25, and a plurality of feed pins 66 are fixed to the feed pin support 66a to project upward at predetermined intervals. The feed pins 66 are respectively engaged with perforations 15c defined by the aligned perforations 11c, 12c and 13c of the sheets 11, 12 and 13. When the feed pin support 66a is moved in the sheet conveying direction, the sheet assembly 25 is conveyed along the first conveying passage 25 by way of engagement of the feed pins 66 with the perforations 15c. Each of the stations at which predetermined operations are performed by ultrasonic welders 51 and 53 and the like is provided, above the first conveying passage 25, with locator pins 67 supported by a locator pin support 67a which is movable up and down. At each station, the feed pin support 66a is moved downward to remove the feed pins 66 away from the perforations 15c, the locator pin support 67a is moved downward onto the sheet assembly 15 to insert the locator pins 67 respectively into locating holes 15b defined by the aligned locating holes 11b, 12b and 13b of the sheets 11, 12 and 13. After the sheet assembly 15 is thus located in each station, the operation to be performed at the station is performed.

The acceptable products 5 pushed onto the second conveying passage 27 by the product take-out device 90 are conveyed along the second conveying passage 27 and transferred to a third conveying passage 28. While the products 5 are conveyed along the third conveying passage 28, predetermined data such as a lot number, date and the like are printed on each product by an ink jet printer 59, and then the print is dried by a drier 61. Then the products are transferred to transfer tables 65 one by one by a transfer arm 63, and further transferred to a depot pallet 100 from the transfer tables 65 by a robot 69 having an arm 68.

The apparatus of this embodiment is controlled by operating switches 26 disposed on the front side thereof.

I claim:

1. A method of continuously assembling chemical analysis slides each including at least two plastic sheets superposed one on another and bonded together, and a chemical analysis film sandwiched therebetween in which while at least two plastic sheets in continuous lengths are conveyed in the longitudinal direction thereof, a plurality of chemical analysis films are sandwiched between the plastic sheets at predetermined intervals, the plastic sheets are bonded together at a portion circumscribing each of the chemical analysis films sandwiched therebetween to form a sheet assembly and individual chemical analysis slides are cut out from the sheet assembly, characterized in that at least one of the sheets in continuous lengths is provided with a plurality of slit means extending in the transverse direction of the sheet at regular intervals at the remaining portions of the sheet which do not form a part of the chemical analysis slide.

2. A method of continuously assembling chemical analysis slides as defined in claim 1 in which a plurality of locating holes are formed in said at least one sheet at the remaining portion, at least one between each pair of slit means.

3. A method of continuously assembling chemical analysis slides as defined in claim 2 in which each of said slit means comprises a plurality of slits extending in the transverse direction of the sheets.

* * * * *